United States Patent [19]

Lunts

[11] Patent Number: 5,149,698
[45] Date of Patent: Sep. 22, 1992

[54] CHLOROANILINE DERIVATIVES

[75] Inventor: Lawrence H. C. Lunts, Broxbourne, England

[73] Assignee: Glaxo Group Limited, London, England

[21] Appl. No.: 624,337

[22] Filed: Dec. 7, 1990

Related U.S. Application Data

[62] Division of Ser. No. 230,358, Aug. 10, 1988, Pat. No. 4,996,218.

Foreign Application Priority Data

Aug. 11, 1987 [GB] United Kingdom ............... 8718939

[51] Int. Cl.$^5$ ............... A61K 31/505; A61K 31/495; C07D 239/26; C07D 239/34
[52] U.S. Cl. ............... 514/211; 514/235.8; 514/227.8; 514/255; 514/256; 540/544; 544/60; 544/122; 544/335
[58] Field of Search ............ 544/335, 122, 60; 514/256, 211, 235.8, 227.8, 255; 540/544

[56] References Cited

U.S. PATENT DOCUMENTS

| | | | |
|---|---|---|---|
| 4,438,128 | 3/1984 | Wiedemann et al. | 514/313 |
| 4,721,717 | 1/1988 | Friebe et al. | 514/274 |
| 4,937,251 | 6/1990 | Lunts | 514/351 |

FOREIGN PATENT DOCUMENTS

| | | |
|---|---|---|
| 303464 | 8/1988 | European Pat. Off. |
| 1178191 | 1/1970 | United Kingdom |
| 2182658 | 10/1986 | United Kingdom |

OTHER PUBLICATIONS

Champion, British Medical Journal, 4 (1973) 730-732.
Kennes et al., Clinical Allergy, 7 (1977) 35-39.
Das et al., British Journal of Dermatology 99 (1978) 197-200.

Primary Examiner—Mukund J. Shah
Assistant Examiner—Matthew V. Grumbling
Attorney, Agent, or Firm—Morgan & Finnegan

[57] ABSTRACT

The invention provides compounds of the general formula (I)

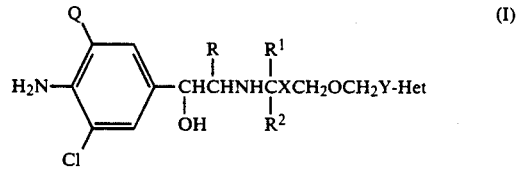

and physiologically acceptable salts and solvates thereof, wherein

Q represents a chlorine atom or a trifluoromethyl group;

X represents a bond, or a $C_{1-6}$alkylene, $C_{2-6}$alkenylene or $C_{2-6}$alkynylene chain, and Y represents a bond, or a $C_{1-6}$alkylene, $C_{2-6}$alkenylene or $C_{2-6}$alkynylene chain with the proviso that the sum total or carbon atoms in the chains X and Y is not more than 10, and the chains $XCH_2$ and $CH_2Y$ may each be optionally substituted by one or two $C_{1-3}$alkyl groups, or, when one carbon atom is substituted by two alkyl groups, these may be linked to form an alkylene group;

R represents a hydrogen atom or a $C_{1-3}$alkyl group;

$R^1$ and $R^2$ each represent a hydrogen atom or a $C_{1-3}$alkyl group, with the proviso that the sum total of carbon atoms in $R^1$ and $R^2$ is not more than 4; and Het is optionally substituted pyrimidinyl.

The compounds have a stimulant action at $\beta$-adrenoreceptors and may be used in the treatment of diseases associated with reversible airways obstruction such as asthma and chronic bronchitis.

11 Claims, No Drawings

CHLOROANILINE DERIVATIVES

This is a divisional of co-pending application Ser. No. 07/230,358 filed Aug. 10, 1988, now U.S. Pat. No. 4,996,218.

This invention relates to chloroaniline derivatives having a stimulant action at $\beta_2$-adrenoreceptors, to processes for their preparation, to pharmaceutical compositions containing them and to their use in medicine.

Chloroaniline derivatives have previously been described as bronchodilators having stimulant activity at $\beta$-adrenoreceptors.

Thus, British Patent Specification No. 1178191 describes compounds of the general structure

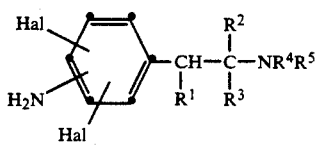

in which the substituents Hal represent bromine or chlorine atoms; $R^1$ represents hydrogen or hydroxyl; $R^2$ and $R^3$ each represent hydrogen or $C_{1-4}$ alkyl; and $R^4$ and $R^5$ each represent hydrogen, $C_{1-6}$ alkyl, alkenyl, alkynyl, hydroxyalkyl, alkoxyalkyl, dialkylaminoalkyl, cycloalkyl, phenyl, benzyl or adamantyl radicals, or $NR^4R^5$ forms a heterocyclic ring optionally substituted by $C_{1-3}$ alkyl groups.

UK Patent Specification Nos. 2165542A and 2182658A describe compounds of the general structure

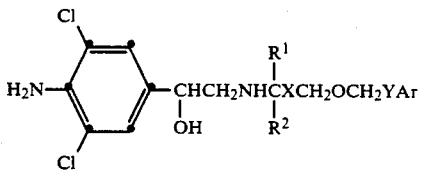

in which $R^1$ and $R^2$ each represent hydrogen or $C_{1-3}$ alkyl; X represents $C_{1-6}$ alkylene, $C_{2-6}$ alkenylene or $C_{2-6}$ alkynylene; Y represents $C_{1-4}$ alkylene, $C_{2-4}$ alkenylene or $C_{2-4}$ alkynylene; and Ar represents a phenyl group optionally substituted by one or more of a variety of specific substituents.

We have now found a novel group of compounds which differ structurally from those described in British Patent Specification No. 1178191 and UK Patent Specification Nos. 2165542A and 2182658A, and which have a desirable and useful profile of activity.

Thus the present invention provides compounds of the general formula (I)

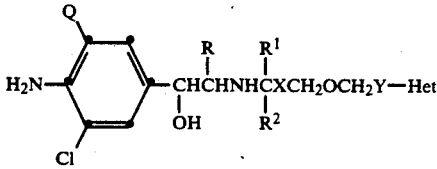

and physiologically acceptable salts and solvates (e.g. hydrates) thereof, wherein Q represents a chlorine atom or a trifluoromethyl group;

X represents a bond, or a $C_{1-6}$ alkylene, $C_{2-6}$ alkenylene or $C_{2-6}$ alkynylene chain, and Y represents a bond, or a $C_{1-6}$ alkylene, $C_{2-6}$ alkenylene or $C_{2-6}$ alkynylene chain with the proviso that the sum total of carbon atoms in the chains X and Y is not more than 10, and the chains $XCH_2$ and $CH_2Y$ may each be optionally substituted by one or two $C_{1-3}$ alkyl groups, or, when one carbon atom is substituted by two alkyl groups, these may be linked to form an alkylene group;

R represents a hydrogen atom or a $C_{1-3}$ alkyl group;

$R^1$ and $R^2$ each represent a hydrogen atom or a $C_{1-3}$ alkyl group, with the proviso that the sum total of carbon atoms in $R^1$ and $R^2$ is not more than 4; and Het represents a benzoheteroaryl or a monocyclic heteroaryl group wherein the heteroaryl group is 5 or 6 membered and contains 1, 2 or 3 hetero atoms, one of which is a nitrogen atom and the other(s) represent nitrogen, oxygen or sulphur atom(s), and the group Het may optionally be substituted by one or two groups selected from $C_{1-4}$ alkyl, $C_{1-4}$ alkoxy, hydroxy, halogen, $-NR^3R^4$ and $-COR^8$;

where $R^3$ and $R^4$ each represent a hydrogen atom or a $C_{1-4}$alkyl group or $-NR^3R^4$ forms a saturated heterocyclic amino group which has 5–7 ring members and optionally contains in the ring one or more atoms selected from $-O-$ or $-S-$ or a group $-NH-$ or $-N(CH_3)-$; and $R^8$ represents hydroxy, $C_{1-4}$ alkoxy or $-NR^3R^4$; with the proviso that (i) when Het represents a pyridyl group substituted by the group $-NR^3R^4$ or $-COR^8$ and Q is a chlorine atom, or (ii) when Het represents a pyridyl group optionally substituted by one or two groups selected from halogen, hydroxy, $C_{1-3}$alkyl and $C_{1-3}$alkoxy, and Y represents a bond or a $C_{1-4}$alkylene, $C_{2-4}$alkenylene or $C_{2-4}$alkynylene chain, then, in both cases, R represents a $C_{1-3}$alkyl group and/or at least one of the chains $-XCH_2-$ and $-CH_2Y-$ is substituted by one or two $C_{1-3}$alkyl groups.

It will be appreciated that the compounds of general formula (I) possess one or more asymmetric carbon atoms. The compounds according to the invention thus include all enantiomers, diastereoisomers and mixtures thereof, including racemates. Compounds in which the carbon atom in the $$-\underset{OH}{CH}-$$

group is in the R configuration are preferred.

In the definition of general formula (I), the term alkenylene includes both cis and trans structures.

In the general formula (I), the chain $XCH_2$ may be for example $-CH_2-$, $-(CH_2)_2-$, $-(CH_2)_3-$, $-(CH_2)_4-$, $-(CH_2)_5-$, $-(CH_2)_6-$, $-(CH_2)_7-$, $-CH_2C\equiv CCH_2-$, $-(CH_2)_2CH=CHCH_2-$, $-(CH_2)_2C\equiv CCH_2-$, $-CH=CH(CH_2)_2-$, $-CH=CH(CH_2)_3-$ or $-CH_2C\equiv C(CH_2)_2-$. The optionally substituted chain $CH_2Y$ may be for example $-CH_2-$, $-(CH_2)_2-$, $-(CH_2)_3-$, $-(CH_2)_4-$, $-(CH_2)_5-$, $-(CH_2)_6-$, $-CH(CH_3)(CH_2)_2-$, $-CH_2CH=CH-$, $-CH_2C\equiv C-$, $-(CH_2)_2CH=CH-$ or $-(CH_2)_2C\equiv C-$.

Preferably the total number of carbon atoms in the chains X and Y is 4 to 10 inclusive. Compounds wherein the sum total of carbon atoms in the chains X and Y is 4, 5, 6, 7, 8 or 9 are particularly preferred.

One preferred group of compounds of formula (I) is that in which X represents a $C_{3-4}$alkylene chain and Y represents a $C_{1-5}$alkylene chain. Particular compounds of this type are those wherein X represents —$(CH_2)_4$— and Y represents —$(CH_2)_2$—, —$(CH_2)_4$ or —$(CH_2)_5$—.

In the compounds of formula (I), R, $R^1$ and $R^2$ may each be, for example, methyl, ethyl, propyl or isopropyl groups. If one of $R^1$ and $R^2$ is a propyl or isopropyl group, the other is a hydrogen atom or a methyl group. R, $R^1$ and $R^2$ are each preferably a hydrogen atom or a methyl group.

A preferred group of compounds are those in which R represents a hydrogen atom.

Another preferred group of compounds are those wherein $R^1$ and $R^2$ are both hydrogen atoms, or $R^1$ is a hydrogen atom and $R^2$ is a $C_{1-3}$ alkyl group, particularly a methyl group, or $R^1$ is a methyl group and $R^2$ is a methyl group.

The group Het is attached to the rest of the molecule through any available position in the heteroaryl ring. Any substituent(s) in the group Het may be at any available position(s) in the benzene and/or the heteroaryl rings. Preferably Het represents a group selected from pyrimidinyl, pyrazinyl, triazinyl, thiazolyl, quinolinyl, benzimidazolyl, benzothiazolyl, benzoxazolyl and pyridyl.

A particularly preferred group of compounds of formula (I) is that in which Het represents a pyrimidinyl or thiazolyl group.

When the group Het is substituted by one or two halogen atoms, these may be chlorine, fluorine or bromine. When —$NR^3R^4$ represents a saturated heterocyclic amino group, this may be, for example, a pyrrolidino, piperidino, hexamethyleneimino, piperazino, N-methylpiperazino, morpholino, homomorpholino or thiamorpholino group.

Preferred compounds according to the invention are
4-amino-3,5-dichloro-α-[[[6-[4-(2-pyrimidinyl)butoxy]-hexyl]amino]methyl] benzenemethanol;
4-amino-3,5-dichloro-α-[[[6-[[6-(5-pyrimidinyl)hexyl-]oxy]hexyl] amino]methyl]benzenemethanol;
4-amino-3,5-dichloro-α-[[[6-[[6-(2-pyrimidinyl)hexyl-]oxy]hexyl] amino]methyl]benzenemethanol;
4-amino-3,5-dichloro-α-[[[6-[3-(2-thiazolyl)propoxy]-hexyl]amino] methyl]benzenemethanol;
and their physiologically acceptable salts and solvates.

Suitable physiologically acceptable salts of the compounds of general formula (I) include acid addition salts derived from inorganic and organic acids, such as hydrochlorides, hydrobromides, sulphates, phosphates, maleates, tartrates, citrates, benzoates, 4-methoxybenzoates, 2- or 4-hydroxybenzoates, 4-chlorobenzoates, benzenesulphonates, p-toluenesulphonates, naphthalenesulphonates, methanesulphonates, sulphamates, ascorbates, salicylates, acetates, diphenylacetates, triphenylacetates, adipates, fumarates, succinates, lactates, glutarates, gluconates, tricarballylates, hydroxy-naphthalenecarboxylates e.g. 1-hydroxy- or 3-hydroxy-2-naphthalenecarboxylates, or oleates. The compounds may also form salts with suitable bases where appropriate. Examples of such salts are alkali metal (e.g. sodium and potassium) and alkaline earth metal (e.g. calcium or magnesium) salts, and salts with organic bases (e.g. triethylamine).

The compounds according to the invention have a stimulant action at $\beta_2$-adrenoreceptors, which further-more is of a particularly advantageous profile. The stimulant action was demonstrated in the isolated trachea of the guinea-pig, where compounds were shown to cause relaxation of contractions induced by $PGF_{2\alpha}$ or electrical stimulation. Compounds according to the invention have shown a particularly long duration of action in these tests.

The compounds according to the invention may be used in the treatment of diseases associated with reversible airways obstruction such as asthma and chronic bronchitis.

The compounds according to the invention are also indicated as useful for the treatment of inflammatory and allergic skin diseases, congestive heart failure, depression, premature labor, glaucoma, and in the treatment of conditions in which there is an advantage in lowering gastric acidity, particularly in gastric and peptic ulceration.

The invention accordingly further provides compounds of formula (I) and their physiologically acceptable salts and solvates for use in the therapy or prophylaxis of diseases associated with reversible airways obstruction in human or animal subjects.

The compounds according to the invention may be formulated for administration in any convenient way. The invention therefore includes within its scope pharmaceutical compositions comprising at least one compound of formula (I) or a physiologically acceptable salt or solvate thereof formulated for use in human or veterinary medicine. Such compositions may be presented for use with physiologically acceptable carriers or excipients, optionally with supplementary medicinal agents.

The compounds may be formulated in a form suitable for administration by inhalation or insufflation, or for oral, buccal, parenteral, topical (including nasal) or rectal administration. Administration by inhalation or insufflation is preferred.

For administration by inhalation the compounds according to the invention are conveniently delivered in the form of an aerosol spray presentation from pressurised packs, with the use of a suitable propellant, such as dichlorodifluoromethane, trichlorofluoromethane, dichlorotetrafluoroethane, carbon dioxide or other suitable gas, or from a nebuliser. In the case of a pressurised aerosol the dosage unit may be determined by providing a valve to deliver a metered amount.

Alternatively, for administration by inhalation or insufflation, the compounds according to the invention may take the form of a dry powder composition, for example a powder mix of the compound and a suitable powder base such as lactose or starch. The powder composition may be presented in unit dosage form in for example capsules or cartridges of e.g. gelatin, or blister packs from which the powder may be administered with the aid of an inhaler or insufflator.

For oral administration, the pharmaceutical composition may take the form of, for example, tablets, capsules, powders, solutions, syrups or suspensions prepared by conventional means with acceptable excipients.

For buccal administration the composition may take the form of tablets, drops or lozenges formulated in conventional manner.

The compounds of the invention may be formulated for parenteral administration by bolus injection or continuous infusion. Formulations for injection may be presented in unit dosage form in ampoules, or in multi-dose containers with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for reconstitution with a suitable vehicle, e.g. sterile pyrogen-free water, before use.

For topical administration the pharmaceutical composition may take the form of ointments, lotions or creasm formulated in a conventional manner, with for example an aqueous or oily base, generally with the addition of suitable thickening agents and/or solvents. For nasal application, the composition may take the form of a spray, formulated for example as an aqueous solution or suspension or as an aerosol with the use of a suitable propellant.

The compounds of the invention may also be formulated in rectal compositions such as suppositories or retention enemas, e.g. containing conventional suppository bases such as cocoa butter or other glyceride.

Where pharmaceutical compositons are described above for oral, buccal, rectal or topical administration, these may be presented in a conventional manner associated with controlled release forms.

A proposed daily dosage of active compound for the treatment of man is 0.005 mg to 100 mg, which may be conveniently administered in one or two doses. The precise dose employed will of course depend on the age and condition of the patient and on the route of administration. Thus a suitable dose for administration by inhalation is 0.005 mg to 20 mg, for oral administration is 0.02 mg to 100 mg, and for parenteral administration is 0.01 mg to 2 mg for administration by bolus injection and 0.01 mg to 25 mg for administration by infusion.

The compounds according to the invention may be prepared by a number of processes. In the following description, Q, X, Y, Het, R, $R^1$ and $R^2$ are as defined for general formula (I) unless otherwise specified. In the preparation of both intermediates and end-products the final step in the reaction may be the removal of a protecting group. Suitable protecting groups and their removal are described in general process (3) below.

In one general process (1), a compound of general formula (I) may be prepared by alkylation. Conventional alkylation procedures may be used.

Thus, for example, in one process (a), a compound of general formula (I) in which $R^1$ is a hydrogen atom may be prepared by alkylation of an amine of general formula (II)

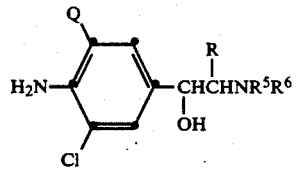
(II)

(wherein $R^5$ is a hydrogen atom or a protecting group and $R^6$ is a hydrogen atom) followed by removal of any protecting group where present.

The alkylation (a) may be effected using an alkylating agent of general formula (III):

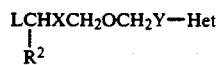
(III)

(wherein L is a leaving group, for example a halogen atom such as chlorine, bromine or iodine, or a hydrocarbylsulphonyloxy group such as methanesulphonyloxy or p-toluenesulphonyloxy).

The alkylation is preferably effected in the presence of a suitable acid scavenger, for example, inorganic bases such as sodium or potassium carbonate, organic bases such as triethylamine, diisopropylethylamine or pyridine, or alkylene oxides such as ethylene oxide or propylene oxide. The reaction is conveniently effected in a solvent such as acetonitrile or an ether e.g. tetrahydrofuran or dioxan, a ketone e.g. butanone or methyl isobutyl ketone, a substituted amide e.g. dimethylformamide or a chlorinated hydrocarbon e.g. chloroform, at a temperature between ambient and the reflux temperature of the solvent.

According to another example (b) of an alkylation process, a compound of general formula (I) in which $R^1$ represents a hydrogen atom may be prepared by alkylation of an amine of general formula (II), as previously defined except that $R^6$ is a hydrogen atom or a group convertible thereto under the reaction conditions, with a compound of general formula (IV):

in the presence of a reducing agent, followed when necessary by removal of any protecting groups.

Examples of suitable $R^6$ groups convertible into a hydrogen atom are arylmethyl groups such as benzyl, α-methylbenzyl and benzhydryl.

Suitable reducing agents include hydrogen in the presence of a catalyst such as platinum, platinum oxide, palladium, palladium oxide, Raney nickel or rhodium, on a support such as charcoal, using an alcohol, e.g. ethanol or methanol, or an ester e.g. ethyl acetate, or an ether e.g. tetrahydrofuran, or water, as reaction solvent, or a mixture of solvents, e.g. a mixture of two or more of those just described, at normal or elevated temperature and pressure, for example from 20° to 100° C. and from 1 to 10 atmospheres.

Alternatively when one or both of $R^5$ and $R^6$ are hydrogen atoms, the reducing agent may be a hydride such as diborane or a metal hydride such as sodium borohydride, sodium cyanoborohydride or lithium aluminium hydride. Suitable solvents for the reaction with these reducing agents will depend on the particular hydride used, but will include alcohols such as methanol or ethanol, or ethers such as diethyl ether or tert-butyl methyl ether, or tetrahydrofuran.

When a compound of formula (II) where $R^5$ and $R^6$ are each hydrogen atoms is used, the intermediate imine of formula (V) may be formed:

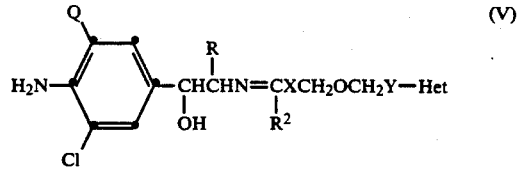
(V)

Reduction of the imine using the conditions described above, followed, where necessary, by removal of any protecting groups, gives a compound of general formula (I).

In another general process (2) compounds of formula (I) may be prepared by reducing an intermediate of general formula (VI):

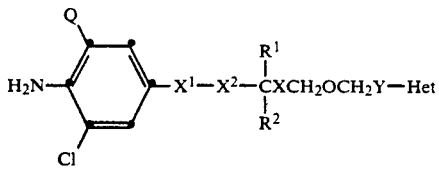 (VI)

wherein at least one of $X^1$, $X^2$, X and Y represents a reducible group and the other(s) take the appropriate meaning as follows, which is $X^1$ is —CH(OH)—, $X^2$ is —CHRNR$^5$— (where R$^5$ represents a hydrogen atom or a protecting group), and X and Y are as defined in formula (I), followed where necessary by removal of any protecting groups.

Suitable reducible groups include those wherein $X^1$ is a group

$X^2$ is a group —CHRNR$^7$— (wherein R$^7$ represents a group convertible to hydrogen by catalytic hydrogenation, for example an arylmethyl group such as benzyl, benzhydryl or α-methylbenzyl).

The reduction may be effected using reducing agents conveniently employed for the reduction of ketones or protected amines.

Thus, for example, when $X^1$ in general formula (VI) represents a

group this may be reduced to a —CH(OH)— group using hydrogen in the presence of a catalyst such as platinum, platinum oxide, palladium, palladium oxide, Raney nickel or rhodium, on a support such as charcoal, using an alcohol e.g. ethanol, an ester e.g. ethyl acetate, an ether e.g. tetrahydrofuran, or water, as reaction solvent, or a mixture of solvents, e.g. a mixture of two or more of those just described, at normal or elevated temperature and pressure, for example from 20° to 100° C. and from 1 to 10 atmospheres. Alternatively, the reducing agent may be, for example, a hydride such as diborane or a metal hydride such as lithium aluminium hydride, sodium bis(2-methoxyethoxy) aluminium hydride, sodium borohydride or aluminium hydride. The reaction may be effected in an appropriate solvent, such as an alcohol e.g. methanol or ethanol, or an ether such as tetrahydrofuran, or a halogenated hydrocarbon such as dichloromethane.

When $X^2$ in general formula (VI) represents a —CHRNR$^7$— group this may be reduced to a —CHRNH— group using hydrogen in the presence of a catalyst as described above.

Where it is desired to use a protected intermediate of general formula (VI) it is particularly convenient to use a protecting group R$^5$ which is capable of being removed under the reducing conditions, for example hydrogen and a catalyst, thus avoiding the need for a separate deprotection step. Suitable protecting groups of this type include arylmethyl groups such as benzyl, benzhydryl and α-methylbenzyl.

In the above reduction process, and also in the preparation of intermediates, care must be taken to avoid the use of hydrogen and a catalyst when products are required in which X and/or Y represent alkenylene or alkynlene groups.

In a further process (3) compounds of formula (I) may be prepared by deprotecting an intermediate of general formula (VII)

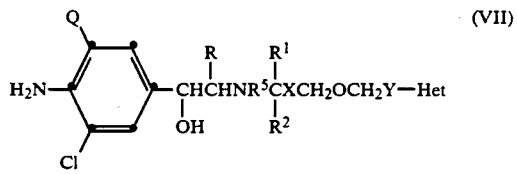 (VII)

wherein R$^5$ is a protecting group and/or the group Het contains a protecting group.

The protecting group may be any conventional protecting group as described for example in "Protective Groups in Organic Chemistry", by Theodora Greene (John Wiley and Sons Inc., 1981). Thus, for example, hydroxy groups may be protected by arylmethyl groups such as benzyl, diphenylmethyl or triphenylmethyl, by acyl groups such as acetyl, or as tetrahydropyranyl derivatives. Examples of suitable amino protecting groups include arylmethyl groups such as benzyl, α-methylbenzyl, diphenylmethyl or triphenylmethyl, and acyl groups such as acetyl, trichloroacetyl or trifluoroacetyl.

The deprotection to yield a compound of general formula (I) may be effected using conventional techniques. Thus for example arylmethyl groups may be removed by hydrogenolysis in the presence of a metal catalyst (e.g. palladium on charcoal). Tetrahydropyranyl groups may be cleaved by hydrolysis under acidic conditions. Acyl groups may be removed by hydrolysis with an acid such as a mineral acid e.g. hydrochloric acid, or a base such as sodium hydroxide or potassium carbonate, and a group such as trichloroacetyl may be removed by reduction with, for example, zinc and acetic acid.

Intermediates of formula (VI) for use in the reduction process (2) in which $X^1$ is the group

may be prepared by reaction of a haloketone of formula (VIII)

 (VIII)

(where Hal represents a halogen atom e.g. bromine) with an amine of formula (IX)

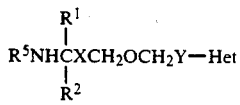

(where $R^5$ is a hydrogen atom or a group convertible thereto by catalytic hydrogenation).

The reaction may be effected in a cold or hot solvent, for example tetrahydrofuran, tert-butyl methyl ether, dioxan, chloroform, dichloromethane, dimethylformamide, acetonitrile, a ketone such as butanone or methylisobutylketone, or an ester such as ethyl acetate, preferably in the presence of a base such as diisopropylethylamine, sodium carbonate or other acid scavenger such as propylene oxide.

Intermediates of general formula (VI) in which $X^1$ is the group

may be reduced to the corresponding intermediate in which $X^1$ is the group —CH(OH)— using for example a metal hydride such as sodium borohydride in a solvent e.g. ethanol, methanol and/or tetrahydrofuran.

Amines of formula (II) and haloketones of formula (VIII) are either known compounds or may be prepared by methods analogous to those described for the preparation of known compounds.

Suitable methods for preparing intermediates of formulae (III), (IV) and (IX) are described in UK Patent Specifications Nos. 2140800A and 2159151A and in the exemplification included hereinafter.

In the general processes described above, the compound of formula (I) obtained may be in the form of a salt, conveniently in the form of a physiologically acceptable salt. Where desired, such salts may be converted to the corresponding free bases using conventional methods.

Physiologically acceptable salts of the compounds of general formula (I) may be prepared by reacting a compound of general formula (I) with an appropriate acid or base in the presence of a suitable solvent such as acetonitrile, acetone, chloroform, ethyl acetate or an alcohol, e.g. methanol, ethanol or isopropanol.

Physiologically acceptable salts may also be prepared from other salts, including other physiologically acceptable salts, of the compounds of general formula (I), using conventional methods.

When a specific enantiomer of a compound of general formula (I) is required, this may be obtained by resolution of a corresponding racemate of a compound of general formula (I) using conventional methods.

Thus, in one example an appropriate optically active acid may be used to form salts with the racemate of a compound of general formula (I). The resulting mixture of isomeric salts may be separated for example by fractional crystallisation, into the diastereoisomeric salts from which the required enantiomer of a compound of general formula (I) may be isolated by conversion into the required free base.

Alternatively, enantiomers of a compound of general formula (I) may be synthesised from the appropriate optically active intermediates using any of the general processes described herein.

Specific diastereoisomers of a compound of formula (I) may be obtained by conventional methods for example, by synthesis from an appropriate asymmetric starting material using any of the processes described herein, or by conversion of a mixture of isomers of a compound of general formula (I) into appropriate diastereoisomeric derivatives e.g. salts which then can be separated by conventional means e.g. by fractional crystallisation.

The following examples illustrate the invention. Temperatures are in °C. 'Dried' refers to drying of organic extracts using magnesium sulphate or sodium sulphate. Unless otherwise stated, thin layer chromatography (t.l.c.) was carried out on silica and flash column chromatography (FCC) on silica (Merck 9385) using one of the following solvent systems: A-toluene:ethanol:0.88 ammonia, B-toluene:ethanol:triethylamine, C-diethyl ether:methanol. The following abbreviations are used: THF—tetrahydrofuran, DMF—dimethylformamide, BTPC—bis(triphenylphosphine)palladium (II) chloride, TAB—tetra-n-butylammonium hydrogen sulphate, DEA—N,N-diisopropylethylamine.

Intermediate 1 is 1-(4-amino-3,5-dichlorophenyl)-2-bromoethanone.

Intermediate 2 is 4-amino-α-(aminomethyl)-3,5-dichlorobenzenemethanol.

Intermediate 3

4-(2-Pyrimidinyl)-3-butynol

A mixture of 2-bromopyrimidine (5.0 g), 3-butynol (2.20 g), dicyclohexylamine (6.87 g), copper (I) iodide (50 mg), BTPC (380 mg) and acetonitrile (50 ml) was stirred at room temperature under nitrogen for 16 h. Ether (150 ml) was added, the mixture filtered and the filtrate evaporated in vacuo. Purification of the residue by FCC eluting with ether and ether-methanol (1–3%) followed by System C (5:1) afforded the title compound as a pale yellow solid (4.29 g) m.p. 58°–64°, t.l.c. (System C, 99:1) Rf 0.08

Intermediate 4

6-(2-Pyrimidinyl)-5-hexynol

A mixture of 2-bromopyrimidine (3.96 g), 5-hexynol (2.44 g), dicylohexylamine (4 g), BTPC (250 mg), copper (I) iodide (25 mg) and acetonitrile (40 ml) was stirred at ambient temperature under nitrogen for 1 h (temp. rose to ~45°). Ether (120 ml) was added, the mixture was filtered and the filtrate was evaporated in vacuo to an oil which was purified by FCC. Elution with ether followed by System C (17:3) gave the title compound as a pale yellow oil (3.64 g), t.l.c. (System C 17:3) Rf 0.34.

Intermediate 5

6-(5-Pyrimidinyl)-5-hexynol

A mixture of 5-bromopyrimidine (3.96 g), 5-hexynol (2.44 g), dicyclohexylamine (4 g) and acetonitrile (50 ml) was de-oxygenated by bubbling nitrogen through the solution for 10 min. BTPC (150 mg) and copper (I) iodide (25 mg) were added and the mixture was heated to 60°–70° under nitrogen for 1 h, cooled and evaporated in vacuo. Ether (175 ml) was added, the mixture filtered and evaporated in vacuo and the residue purified by FCC. Elution with ether followed by System C (19:1–92:8) gave the title compound as a pale yellow oil (3.79 g), t.l.c. (System C (17:3) Rf 0.55.

Intermediate 6

2-Pyrimidinebutanol 4-(2-Pyrimidinyl)-3-butynol (1.5 g) in ethanol (40 ml) was added to pre-reduced 10% palladium on charcoal (50% aqueous paste) in ethanol (60 ml) and hydrogenated at room temperature and atmospheric pressure. The catalyst was removed by filtration through hyflo and the solvent evaporated in vacuo. The residual oil was purified by FCC. Elution with System C (19:1) and (9:1) gave the title compound as a pale yellow oil (1.32 g)

Analysis: Found: C, 63.1; H, 7.7; N, 18.1. $C_8H_{12}N_2O$ requires C, 63.1; H, 7.95; N, 18.4%.

Intermediate 7

2-Pyrimidinehexanol

A solution of 6-(2-pyrimidinyl)-5-hexynol (3.09 g) in ethanol (100 ml) was added to a pre-hydrogenated suspension of 10% palladium on charcoal (1.05 g) in ethanol (50 ml) and hydrogenated at room temperature and pressure, filtered and evaporated in vacuo. The residual oil was purified by FCC eluting with ether and System C (99:1–85:15) to give the title compound as a pale yellow oil (0.93 g).

Analysis: Found: C,66.4; H,9.1; N,15.6; $C_{10}H_{16}N_2O$ requires C,66.6; H,8.95; N,15.5%.

Intermediate 8

5-Pyrimidinehexanol

A solution of 6-(5-pyrimidinyl)-5-hexynol (3.52 g) in ethanol (20 ml) was added to a pre-hydrogenated suspension of 10% palladium on carbon (1 g) in ethanol (130 ml) and hydrogenated at room temperature and pressure. The mixture was filtered through hyflo and the filtrate evaporated in vacuo to give the title compound as a pale yellow oil (3.38 g).

Analysis: Found: C,66.6; H,9.0; N,15.2; $C_{10}H_{16}N_2O$ requires C,66.6; H,8.95; N,15.5%.

Intermediate 9

1-(Phenylmethyl)-2-benzimidazolepropanol

A mixture of 2-benzimidazolepropanol (3.52 g), benzyl bromide (2.38 ml) and anhydrous potassium carbonate (5.52 g) in acetonitrile (57 ml) was stirred at reflux for 4 h, after which time more benzyl bromide (0.24 ml) was added. The mixture was stirred at reflux for a further 2 h, cooled, diluted with water (200 ml), extracted with ethyl acetate (2×100 ml) and the organic extracts dried and evaporated in vacuo to give an orange oil. Purification by FCC eluting with System B (98:2:1) gave a colourless oil (4.3 g) which solidified on standing to give the title compound as a white solid (4.3 g), t.l.c. (System A 40:10:1) Rf 0.41.

Intermediate 10

2-Benzoxazoleethanol

A mixuture of 2-methylbenzoxazole (4.0 g) and paraformaldehyde (1.35 g) was heated at 140° with stirring in a 25 ml autoclave for 3 h. The mixture was cooled and the residue purified by FCC. Elution with hexane-ether (2:1–1:1) followed by ether and ether-methanol (1–5%) afforded a product (1.8 g) which was distilled b.p. 165°–170°/0.4 mmHg (Kugelrohr) to give the title compound as a colourless solid (1.226 g) m.p. 47°–52°, t.l.c. (ether) Rf 0.73.

Intermediate 11

2-[4-[(6-Bromohexyl)oxy]butyl]pyrimidine

A mixture of 2-pyrimidinebutanol (1.31 g), 1,6-dibromohexane (5 ml), 50% aqueous sodium hydroxide solution (5 ml) and TAB (140 mg) was vigorously stirred under nitrogen at 23° for 20 h. Ether (25 ml) and water (20 ml) were added, the organic phase separated, washed with brine (20 ml), dried and evaporated in vacuo. The residue was purified by FCC. Elution with hexane and hexane-ether (9:1) followed by ether afforded the title compound as a colourless oil (1.67 g)

Analysis: Found: C,53.3; H,7.2; N,8.9. $C_{14}H_{23}BrN_2O$ requires C,53.3; H,7.35; N,8.9%.

Intermediate 12

4-[2-[(6-Bromohexyl)oxy]ethyl]-2-methylthiazole

A mixture of 2-methyl-4-thiazoleethanol (2.22 g), 1,6-dibromohexane (7.1 ml) 12.5M aqueous sodium hydroxide (4 ml) and TAB (0.1 g) was stirred rapidly at room temperature for 16 h. The reaction mixture was diluted with water (30 ml), extracted with ether (3×30 ml) and the combined organic extracts were washed with water (30 ml) and brine (30 ml), dried and concentrated. The residual oil was purified by FCC eluting with diethyl ether-hexane (1:3) to give the title compound as an orange oil (2.21 g), t.l.c. (ether-hexane 1:3) Rf 0.17

Intermediate 13

2-[2-[(6-Bromohexyl)oxy]ethyl]benzoxazole

A mixture of 2-benzoxazoleethanol (1.46 g), 50% sodium hydroxide (3 ml), 1,6-dibromohexane (3 ml), TAB (100 mg) and dichloromethane (2 ml) was vigorously stirred at room temperature for 22 h, diluted with water (15 ml) and extracted with ether (40 ml). The organic phase was washed with brine (10 ml), dried and evaporated in vacuo. The residual oil was purified by FCC. Elution with hexane and hexane-ether (19:1) followed by hexane-ether (2:1) and ether gave the title compound as a pale yellow oil (1.60 g) which solidified on refrigeration.

Analysis: Found: C,54.8; H,6.0; N,4.35. $C_{15}H_{20}BrNO_2$ requires C,55.2; H,6.2; N,4.3%.

Intermediate 14

2-[6-[(6-Bromohexyl)oxy]hexyl]pyrimidine

A mixture of 2-pyrimidinehexanol (1.18 g), 1,6-dibromohexane (4 ml), 50% sodium hydroxide (4 ml) and TAB (100 mg) was vigorously stirred at room temperature for 17 h, then diluted with water (40 ml) and ether (50 ml). The organic phase was dried and evaporated in vacuo to an oil which was purified by FCC. Elution with hexane followed by hexane-ether (1:1) gave the title compound as a colourless oil (670 mg), t.l.c. (ether) Rf 0.24

Intermediate 15

5-[6-[(6-Bromohexyl)oxy]hexyl]pyrimidine

A mixture of 5-pyrimidinehexanol (1.82 g), 50% sodium hydroxide (6 ml), 1,6-dibromohexane (6 ml) and TAB (150 mg) was vigorously stirred at room temperature for 30 h then diluted with water (20 ml) and ether (25 ml). The organic phase was dried and evaporated in vacuo. The residue was purified by FCC eluting with hexane followed by hexane-ether (1:1) and ether, to give the title compound as a colourless liquid (2.21 g), t.l.c. (ether) Rf 0.35.

Intermediate 16

2-[2-[(5-Bromopentyl)oxy]ethyl]quinoline 2-(2-Hydroxyethyl)quinoline (2.00 g), TAB (200 mg) and 1,5-dibromopentane (8 ml) were dissolved in dichloromethane (6 ml) and 50% aqueous sodium hydroxide (8 ml) added. The mixture was vigorously stirred at room temperature for 24 h, diluted with water (50 ml) and extracted with diethyl ether (2×30 ml). The organic extracts were dried, filtered and evaporated in vacuo to afford an oil, which was purified by FCC eluting with cyclohexane-ether (1:1) and ether, to give the title compound as a yellow oil (2.67 g), t.l.c. (ether) Rf 0.40.

Intermediate 17

2-[3-[(5-Bromopentyl)oxy]propyl]-1-(phenylmethyl)-benzimidazole

A mixture of 1-(phenylmethyl)-2-benzimidazole-propanol (3.0 g), 1,5-dibromopentane (7.77 g), TAB (0.5 g) and 40% sodium hydroxide (5 ml) in dichloromethane (10 ml) was stirred at room temperature for 6 h under nitrogen. The mixture was diluted with water (100 ml) and extracted with dichloromethane (2×100 ml). The dried extracts were evaporated in vacuo to give an oil. Purification by FCC eluting with hexane-ether (10:0→0:10) gave the title compound as a colourless oil (0.98 g).
Analysis: Found: C,63.30; H,6.54; N,6.76. $C_{22}H_{27}BrN_2O$ requires C,63.61; H,6.55; N,6.74%.

Intermediate 18

2-[3-[(5-Bromopentyl)oxy]propyl]-1H-benzimidazole

A solution of 2-[3-[(5-bromopentyl)oxy]propyl]-1-(phenylmethyl) benzimidazole (1.7 g) in absolute ethanol (20 ml) containing 1:9 conc. hydrochloric acid:ethanol (3.27 ml) was hydrogenated over pre-reduced 10% palladium oxide on charcoal catalyst (300 mg) in ethanol (5 ml) until the uptake of hydrogen (101 ml) ceased. The mixture was filtered through hyflo and evaporated in vacuo to give an oil, which was dissolved in ether (150 ml) and washed with 8% sodium bicarbonate solution (100 ml), dried and evaporated in vacuo to give an oil. Purification by FCC eluting with hexane-ether (2:3→0:5) gave the title compound as a yellow oil (0.92 g).
Analysis: Found: C,55.1; H,6.55; N,8.6. $C_{15}H_{21}BrN_2O$ requires C,55.4; H,6.5; N,8.6%.

Intermediate 19

N-[6-[2-(2-Benzoxazolyl)ethoxy]hexyl]benzenemethanamine

A solution of 2-[2-[(6-bromohexyl)oxy]ethyl]benzoxazole (1.55 g) in benzylamine (6 ml) was heated at 125° for 2 h under nitrogen, cooled, diluted with ether (100 ml) and the ether suspension washed with 8% sodium bicarbonate solution (25 ml). The organic phase was dried and evaporated in vacuo. Benzylamine was removed by bulb to bulb distillation (b.p. 130°/25 mm) to leave a product which was purified by chromatography over silica (Merck 60) eluting with System B (89:10:1) to afford the title compound as a red oil (250 mg), t.l.c. (System A 39:10:1) Rf 0.55.

Intermediate 20

4-Amino-3,5-dichloro-α-[[[6-[2-(2-benzoxazolyl)ethoxy]hexyl](phenylmethyl)amino]methyl]benzenemethanol A solution of Intermediate 1 (1.16 g), N-[6-[2-(2-benzoxazolyl) ethoxy]hexyl]benzenemethanamine (1.46 g) and DEA (0.78 ml) in THF (50 ml) was allowed to stand for 6 h, then filtered and evaporated in vacuo. The residual gum in methanol (20 ml) was cooled to 0°-5° and sodium borohydride (650 mg) added portionwise over 0.5 h. After a further 0.5 h at 5° the solution was evaporated in vacuo and the residue partitioned between water (30 ml) and ethyl acetate (60 ml). The organic phase was dried and evaporated in vacuo to a gum. The residue was purified by FCC eluting with hexane-ethyl acetate-triethylamine (60:40:1) to give the title compound as a pale yellow oil (1.10 g), t.l.c. (hexane-ethyl acetate 2:1) Rf 0.21.

Intermediate 21

2-[2-[(6-Bromohexyl)oxy]ethyl]pyridine

A mixture of 2-pyridineethanol (5 g), 1,6-dibromohexane (20 ml), 50% (w/v) sodium hydroxide (20 ml) and TAB (500 mg) was stirred at room temperature for 6 h. Water (100 ml) was added and the mixture was extracted with ether (2×100 ml). The organic extracts were washed with water and brine, dried and concentrated to an oil which was purified by FCC eluting with hexane→hexane-ether (1:1) to give the title compound as a colourless oil (6.6 g), t.l.c. (hexane-ether 1:1) Rf 0.19.

Intermediate 22

N-[6-[2-(2-Pyridinyl)ethoxy]hexyl]benzenemethanamine

2-[2-[(6-Bromohexyl)oxy]ethyl]pyridine (6.3 g) was added to benzylamine (20 ml) at 140° under nitrogen. After 1 h at 140° the reaction mixture was cooled and partitioned between 2M sodium hydroxyde (100 ml) and ether (100 ml). The organic layer was washed with water and brine, dried and concentrated to a yellow oil. The excess benzylamine was removed by distillation under reduced pressure to leave the title compound as a yellow oil (6.8 g), t.l.c. (System A 80:20:2) Rf 0.44.

Intermediate 23

4-Amino-3,5-dichloro-α-[1-[(phenylmethyl)[6-[2-(2-pyridinyl)ethoxy]hexyl]amino]ethyl]benzenemethanol A solution of 1-(4-amino-3,5-dichlorophenyl)-2-bromopropanone (1.12 g), N-[6-[2-(2-pyridinyl)ethoxy]hexyl]benzenemethanamine (1.18 g) and DEA (0.92 ml) in THF (20 ml) was heated at reflux for 20 h under nitrogen, then cooled to 0°-5° for 1 h. The mixture was filtered and the filtrate evaporated in vacuo to a dark oil which was taken up in methanol (20 ml) and cooled to 0°-5°. Sodium borohydride (570 mg) was added portionwise over 20 min, the solution allowed to warm to 20° over 2 h and evaporated in vacuo. The residue was partitioned between water (50 ml) and ethyl acetate (100 ml) and the organic phase dried and evaporated in vacuo to a gum. Purification by FCC eluting with hexane-ethyl acetate (2:1-1:1) gave the title compound as a colourless gum (680 mg), t.l.c. (hexane-ethyl acetate 2:1) Rf 0.15.

Intermediate 24

α-Methyl-2-pyridinepropanol

Dimethyl sulphoxide (3.3 ml) was added dropwise to a solution of oxalyl chloride (3.9 ml) in dichloromethane (25 ml) at −78° under nitrogen. After gas evolution had ceased (5 min) a solution of 2-pyridinepropanol (4.0 g) in dichloromethane (20 ml) was added over 5 min and the solution stirred at −78° for 20 min. Triethylamine (5 ml) was added dropwise to the solution, then the resulting dark green mixture warmed to 20° and washed with 2M sodium carbonate solution (20 ml). The organic phase was dried and evaporated in vacuo to give 2-pyridinepropanal. This aldehyde was immediately dissolved in THF (30 ml) and added dropwise to a 3M solution of methylmagnesium chloride in THF (20 ml) at 0°-5° under nitrogen. After 1 h, water (10 ml) was cautiously added followed by sufficient 2M hydrochloric acid to dissolve all the magnesium residues (resulting pH ∼7). The solution was extracted with dichloromethane (3×30 ml) and the organic extracts dried and evaporated in vacuo to a dark oil. Kugelrohr bulb to bulb distillation (b.p. 130°-135°/0.7 mm) afforded the title compound as a pale yellow oil (0.91 g), t.l.c. ethyl acetate Rf 0.17.

Intermediate 25

N-[6-[1-Methyl-3-(2-pyridinyl)propoxy]hexyl]benzenemethanamine

A mixture of α-methyl-2-pyridinepropanol (0.62 g) 1,6-dibromohexane (4 ml), 50% sodium hydroxide (4 ml) and TAB (50 mg) was vigorously stirred at 50° for 6 h, cooled and diluted with water (15 ml) and ether (100 ml). The ether extract was dried and evaporated in vacuo to an oil which was partitioned between 2N hydrochloric acid (60 ml) and hexane (2×25 ml). The acidic aqueous phase was basified with 40% sodium hydroxide to pH12 and extracted with ether (2×50 ml). The ethereal extracts were dried and evaporated in vacuo to give 2-[3-[(6-bromohexyl)oxy]-1-methylpropyl]pyridine (360 mg) as a colourless oil. This was dissolved in benzylamine (4 ml), and heated at 125° for 2 h under nitrogen, cooled and combined with an earlier reaction product (from 0.28 g of the bromo compound) and partitioned between 8% sodium bicarbonate solution (40 ml) and ether (100 ml). The ether phase was dried and evaporated in vacuo. Benzylamine was removed by distillation in vacuo (Kugelrohr 150°/25 mm) to leave the title compound as a yellow oil (0.68 g), t.l.c. (System A 39:10:1) Rf 0.36.

Intermediate 26

4-Amino-3,5-dichloro-α-[[[6-[1-methyl-3-(2-pyridinyl)propoxy]hexyl](phenylmethyl)amino]methyl]benzenemethanol A solution of Intermediate 1 (0.6 g) and DEA (0.55 ml) in THF (20 ml) was treated with N-[6-[1-methyl-3-(2-pyridinyl)propoxy]hexyl]benzenemethanamine (0.72 g) and the solution allowed to stand for 7 h, then filtered and evaporated in vacuo. The residue in methanol (15 ml) was cooled to 0°-5° and sodium borohydride (0.42 g, 11.1 mmol) added portionwise over 20 min. After 1 h, the solution was evaporated in vacuo and the residue partitioned between water (15 ml) and ethyl acetate (60 ml). The organic phase was washed with brine (10 ml), dried and evaporated in vacuo to a pale yellow gum which was purified by FCC eluting with hexane-ethyl acetate-triethylamine (66:33:1) to give the title compound as a pale yellow gum (0.91 g), t.l.c. (diethyl ether) Rf 0.38.

Intermediate 27

[6-[(6-Bromohexyl)oxy]-1-hexynyl]pyrazine

A mixture of bromopyrazine (1.64 g), 6-[(6-bromohexyl)oxy]-1-hexyne (2.69 g) N,N-dicyclohexylamine (1.88 g), BTPC (130 mg) and copper (I) iodide (13 mg) in acetonitrile (30 ml) was stirred at 22° under nitrogen for 1 h. Ether (150 ml) was added, the mixture filtered and evaporated in vacuo to an oil which was purified by FCC eluting with hexane-ether (3:2→1:1) followed by ether to give the title compound as a dark yellow oil (2.79 g), t.l.c. (ether) Rf 0.5.

Intermediate 28

[6-[(6-Bromohexyl)oxy]hexyl]pyrazine

A solution of [6-[(6-bromohexyl)oxy]-1-hexynyl]pyrazine (2.76 g) in ethanol (70 ml) was added to a pre-hydrogenated suspension of 10% palladium on carbon (2.00 g) in ethanol (50 ml) and hydrogenated at room temperature and pressure for 11 h. The mixture was filtered through hyflo and evaporated in vacuo to afford the title compound as a colourless oil (2.45 g), t.l.c. (ether) Rf 0.55.

Intermediate 29

3-[(2-Thiazolyl)]-2-propynol

Copper (I) iodide (28.5 mg) was added to a stirred solution of 2-bromothiazole (5 g), propargyl alcohol (1.68 g), BTPC (210 mg) and DEA (2.41 g) in acetonitrile (88 ml). The mixture was stirred under nitrogen for 80 h, concentrated and partitioned between ethyl acetate (100 ml) and water (100 ml). The organic layer was dried and concentrated to yield the crude product which was purified by FCC eluting with toluene/ethyl acetate (5:2) to give the title product as a brown oil (0.68 g), t.l.c. (toluene/ethyl acetate 2:1) Rf 0.27.

Intermediate 30

2-Thiazolepropanol

Glacial acetic acid (16 ml) was added dropwise during 0.25 h to a stirred solution of 3-(2-thiazolyl)-2-propynol (2.4 g) and dipotassium azodicarboxylate (50 g) in pyridine (200 ml). The mixture was stirred at room temperature for 1 h and additional glacial acetic acid (40 ml) added during 0.5 h. The mixture was stirred at room temperature for 2 days. The solvent was removed by azeotropic distillation with toluene (2×100 ml) and the residue partitioned between water (100 ml) and ethyl acetate (100 ml). The aqueous layer was extracted with ethyl acetate (2×50 ml) and the combined extracts dried and evaporated to leave a brown oil. This was purified by FCC eluting with toluene:ethyl acetate:triethylamine (50:50:1) to give the title compound as an orange oil (1.45 g), t.l.c. (toluene:ethyl acetate:triethylamine 50:50:1) Rf 0.15.

Intermediate 31

2-[[(6-Bromohexyl)oxy]propyl]thiazole

A mixture of 2-thiazolepropanol (1.45 g) 1,6-dibromohexane (7.4 g), TAB (125 mg) and 50% w/v sodium hydroxide solution (5 ml) was stirred at room temperature for 6 h, diluted with water (50 ml) and extracted with ether (3×50 ml). The combined, dried extracts were evaporated and the residue was purified by FCC eluting with toluene followed by System B (98:2:1), to give the title compound as a pale yellow oil (1.76 g), t.l.c. (System B 95:5:1) Rf 0.55.

Intermediate 32

6-[(6-Bromohexyl)oxy]-1-hexyne

A mixture of 5-hexyn-1-ol (5 g), 1,6-dibromohexane (37.29 g), TAB (1 g) and 50% sodium hydroxide solution (20 ml) was stirred under nitrogen for 22 h. The mixture was diluted with water (100 ml) and extracted with diethyl ether (2×150 ml). The combined organic extracts were dried and evaporated in vacuo to give an oil. Purification by FCC eluting with hexane followed by hexane:ether (95:5) gave the title compound as a colourless oil. (7.7 g), t.l.c. (hexane:ether 2:1) Rf 0.80.

Intermediate 33

2-[6-[(6-Bromohexyl)oxy]-1-hexynyl]quinoline

A mixture of 2-bromoquinoline (3.00 g), 6-[(6-bromohexyl)oxy]-1-hexyne (3.77 g), BTPC (90 mg), copper (I) iodide (11 mg) and dicyclohexylamine (2.79 g) in acetonitrile (35 ml) was stirred at room temperature under nitrogen for 20 h. The mixture was diluted with ether (90 ml), filtered and the filtrate evaporated in vacuo to give a brown oil. Purification by FCC eluting with hexane:ether (4:1→2:1) gave the title compound as a brown oil (4.25 g), t.l.c. (hexane:ether 2:1) Rf 0.22.

Intermediate 34

N-[6-[[6-(2-Pyridinyl)-5-hexynyl]oxy]hexyl]benzenemethanamine

A mixture of 2-bromopyridine (2.67 g), 6-[(6-bromohexyl)oxy]-1-hexyne (4.41 g), BTPC (105 mg), copper (I) iodide (13 mg) and N,N-dicyclohexylamine (3.37 g) in acetonitrile (40 ml) was stirred at room temperature under nitrogen for 20 h. The mixture was diluted with ether (100 ml), filtered and the filtrate evaporated in vacuo to give a brown oil. Purification by FCC eluting with hexane:ether (9:1→1:1) gave a brown oil (4.59 g) which was heated with benzylamine (13.8 ml) at 100° for 2.5 h. The mixture was washed with 8% sodium bicarbonate solution (75 ml) and ether (75 ml). The combined organic extracts were dried and evaporated in vacuo and excess benzylamine was removed by distillation in the Kügelrohr apparatus to leave the title compound as a brown oil (3.60 g), t.l.c. (System A 40:10:1) Rf 0.58.

Intermediate 35

4-Amino-3,5-dichloro-α-[[(phenylmethyl)][6-(2-pyridinyl)-5-hexynyl]oxy]hexyl]amino]methyl]benzenemethanol A solution of 1-[4-amino-3,5-dichloro]-2-bromoethanone (0.93 g) and N-[6-[[6-(2-pyridinyl)-5-hexynyl]oxy]hexyl]benzenemethanamine (1.2 g) in THF (30 ml) was stirred under nitrogen for 20 h. The mixture was filtered and the filtrate evaporated in vacuo to give an oil. The oil was dissolved in methanol (25 ml) and dichloromethane (35 ml) and sodium borohydride (0.51 g) added portionwise to the solution at 0° under nitrogen. The solution was stirred at room temperature for 1 h, then carefully diluted with water (12 ml) and evaporated in vacuo. The residue was partitioned between ethyl acetate (100 ml) and water (100 ml), the aqueous phase was re-extracted with ethyl acetate (100 ml) and the combined organic fractions dried and evaporated in vacuo to give a brown oil. Purification by FCC eluting with hexane:ethyl acetate (1:1) gave the title compound as an orange-brown oil (1.65 g), t.l.c. (hexane:ethyl acetate 1:1on 2% triethylamine doped plate) Rf 0.61.

Intermediate 36

2-[3-[(6-Bromohexyl)oxy]propyl]quinoline

2-Quinolinepropanol (0.92 g), 50% aqueous sodium hydroxide (5 ml), 1,6-dibromohexane (5 ml) and TAB (57 mg) were vigorously stirred at 21° for 6 h. The mixture was diluted with water (25 ml) and ether (100 ml) and the organic phase dried and evaporated in vacuo. The residue was purified by FCC with hexane eluant to remove 1,6-dibromohexane. Elution with ether afforded the title compound as a yellow oil (0.88 g), t.l.c. ether Rf 0.51.

EXAMPLE 1

4-Amino-3,5-dichloro-α-[[[6-[4-(2-pyrimidinyl)butoxy]-hexyl]amino]methyl]benzenemethanol A mixture of Intermediate 2 (0.84 g), 2-[4-[(6-bromohexyl)oxy]butyl]pyrimidine (0.80 g), DEA (0.53 ml) and DMF (10 ml) was heated at 100° for 1 h under nitrogen. The solution was cooled, evaporated in vacuo, and the residue purified by FCC eluting with System A (88:10:1). The resulting product was dissolved in hot isopropanol (15 ml) containing fumaric acid (90.5 mg), cooled and kept at 0° for 1 h. The crystalline, hygroscopic hemifumarate salt was collected by filtration. The mother liquors deposited a second crop which was combined with the first crop, and partitioned between 8% sodium bicarbonate solution (60 ml) and ethyl acetate (2×60 ml). The combined organic extracts were dried and evaporated in vacuo to a gum. Trituration with hexane (20 ml) for 24 h afforded the title compound as a colourless powder (440 mg), m.p. 77°–79°, t.l.c. (System A 39:10:1) Rf 0.46.

Analysis: Found: C,57.5; H,7.2; N,12.0; Cl,15.6. $C_{22}H_{32}Cl_2N_4O_2$ requires C,58.0; H,7.1; N,12.3; Cl,15.6%.

Examples 2–4 were prepared in a similar manner from Intermediate 2 and the appropriate bromo compound.

EXAMPLE 2

4-Amino-3,5-dichloro-α-[[[5-(2-quinolinylethoxy)pentyl]amino]methyl]benzenemethanol, (E)-butenedioate salt (2:1)

From Intermediate 2 (1.00 g) and 2-[2-[(5-bromopentyl)oxy]ethyl]quinoline (0.97 g). The product from FCC (eluting with System A (44:5:1) and (39:10:1)) was dissolved in ethyl acetate (60 ml), washed with 8% sodium bicarbonate solution (30 ml), brine (30 ml), dried and evaporated in vacuo. The residual gum (~1 g) was dissolved in hot isopropanol (12 ml) and treated with fumaric acid (125 mg). The hot solution was filtered and the crystals which deposited on cooling were collected by filtration. A further recrystallisation from isopropanol (20 ml) afforded the title compound (0.71 g) m.p. 140°–143° (after being dried at 50°/1 mm Hg for 6 h.), t.l.c. (System A 39:10:1) Rf 0.52.

Analysis: Found: C,58.9; H,5.9; N,7.65; Cl, 14.2. $C_{24}H_{29}Cl_2N_3O_2.0.5C_4H_4O_4.0.05C_3H_8O.0.4H_2O$ requires C,59.2; H,6.1; N,7.9% Cl,13.4%.

EXAMPLE 3

4-Amino-3,5-dichloro-α-[[[6-[2-(2-methyl-4-thiazolyl)ethoxy]hexyl]amino]methyl]benzenemethanol From 4-[2-[(6-bromohexyl)oxy]ethyl]-2-methylthiazole (1.2 g) and Intermediate 2 (1.30 g), heating the reaction mixture for 1.5 hr. FCC eluting with System B (97:3:1) gave an oil which when triturated with hexane gave the title compound as a white solid (0.78 g) m.p. 67°-69°.

Analysis: Found: C,53.9; H,6.6; N,9.3; Cl,15.7; S,7.2. $C_{20}H_{29}Cl_2N_3O_2S$ requires C,53.8; H,6.6; N,9.4; Cl,15.9; S,7.2%

EXAMPLE 4

4-Amino-3,5-dichloro-α-[[[5-[3-(1H-benzimidazol-2-yl)propoxy]pentyl]amino]methyl]benzenemethanol, (E)-butenedioate salt (2:1)

From Intermediate 2 (0.87 g), and 2-[3-[(5-bromopentyl)oxy]propyl]-1H-benzimidazole (0.85 g), heating the reaction mixture for 3 h. FCC eluting with System B (95:5:1) gave a brown oil which was dissolved in methanol (15 ml) and treated with fumaric acid (0.08 g). The solution was evaporated and triturated with diethyl ether to give an orange solid. Treatment with hot isopropanol-ether (ca 1:4) followed by evaporation in vacuo gave a yellow foam, which was dried in vacuo at ca 40° for 10 h to give the title compound as a yellow solid (335 mg) m.p. 55°-60° (decomp), t.l.c. (System A 40:10:1) Rf 0.51.

EXAMPLE 5

4-Amino-3,5-dichloro-α-[[[6-[[6-(2-pyrimidinyl)hexyl]oxy]hexyl]amino]methyl]benzenemethanol A mixture of Intermediate 2 (0.66 g), 2-[6-[(6-bromohexyl)oxy]hexyl]pyrimidine (0.66 g), DEA (0.64 ml) and DMF (14 ml) was heated at 90° for 4 h, cooled and evaporated in vacuo. The oily residue was purified by FCC with System B (94:5:1) to give a product (705 mg), which was dissolved in methanol (7 ml) and fumaric acid (85 mg) added. The solution was evaporated in vacuo and the residue triturated with dry ether causing crystallisation, then recrystallised from isopropanol (7 ml). The hygroscopic crystals were rapidly collected by filtration and partitioned between ethyl acetate (75 ml) and 8% sodium bicarbonate solution (25 ml). The organic phase was dried and evaporated in vacuo to give a gum which was further purified by FCC eluting with System B (96:3:1-94:5:1) to give a gum. Trituration with hexane afforded the title compound as a colourless powder (320 mg) m.p. 55°-57°.

Analysis: Found: C,59.5; H,7.6; N,11.4; Cl,14.8. $C_{24}H_{36}Cl_2N_4O_2$ requires C,59.6; H,7.5; N,11.6; Cl,14.7%.

EXAMPLE 6

4-Amino-3,5-dichloro-α-[[[6-[[6-(5-pyrimidinyl)hexyl]oxy]hexyl]amino]methyl]benzenemethanol Intermediate 2 (1.33 g) and 5-[6-[(6-bromohexyl)oxy]hexyl]pyrimidine (1.32 g) were dissolved in DMF (22 ml) containing DEA (1.02 ml) and heated at 100°-110° for 2 h, cooled and evaporated in vacuo. The residue was purified by FCC. Elution with toluene and System B (97:2:1-94:5:1) followed by System B (89:10:1) gave the desired product (380 mg) followed by mixed fractions. The mixed fractions were dissolved in methanol (6 ml) and fumaric acid (80 mg) added, then the solution evaporated in vacuo. The oily residue was slowly recrystallised from isopropanol (~10 ml) to afford the hygroscopic fumarate salt, which was taken up in methanol (~3 ml) and partitioned between 8% sodium bicarbonate solution (15 ml) and ethyl acetate (50 ml). The organic phase was dried and evaporated in vacuo to give the product as a gum, which was combined with the desired product obtained above. Trituration with hexane afforded the title compound as a pale yellow powder (620 mg) m.p. 59°-61°, t.l.c. (System A 80:20:1) Rf 0.47.

EXAMPLE 7

4-Amino-3,5-dichloro-α-[[[6-[2-(2-benzoxazolyl)ethoxy]hexyl]amino]methyl]benzenemethanol A solution of 4-amino-3,5-dichloro-α-[[[6-[2-(2-benzoxazolyl)ethoxy]hexyl](phenylmethyl)amino]methyl]benzenemethanol (1.09 g) in ethanol (25 ml) containing conc. hydrochloric acid-ethanol (1:9, 1.78 ml) was added to a pre-hydrogenated suspension of 10% palladium on carbon (50% aqueous paste, 0.65 g) and hydrogenated at room temperature and pressure, then filtered through hyflo and evaporated in vacuo. The residue was partitioned between 8% sodium bicarbonate (25 ml) and ethyl acetate (50 ml) and the organic phase dried and evaporated in vacuo to a semi solid. Purification by FCC over silica (Merck 60) eluting with System B (97:2:1→94:5:1) afforded the title compound as a gum, which crystallised after trituration with hexane to a white solid (613 mg) m.p. 85°-87°.

Analysis: Found: C,59.1; H,6.2; N,8.85; Cl,15.25; $C_{23}H_{29}Cl_2N_3O_3$ requires C,59.2; H,6.3; N,9.0; Cl,15.2%.

EXAMPLE 8

4-Amino-3,5-dichloro-α-[1-[[6-[2-(2-pyridinyl)ethoxy]hexyl]amino]ethyl]benzenemethanol, (E)-butenedioate salt (2:1)

A solution of 4-amino-3,5-dichloro-α-[1-[(phenylmethyl)[6-[2-(2-pyridinyl)ethoxy]hexyl]amino]ethyl]benzenemethanol (0.67 g) in ethanol (25 ml) containing conc. hydrochloric acid-ethanol (1:9, 2.33 ml) was added to a prehydrogenated suspension of 10% palladium on charcoal (50% aqueous paste, 1 g) in ethanol (20 ml) and hydrogenated at room temperature and pressure. The mixture was filtered through hyflo and evaporated in vacuo to an oil which was partitioned between 8% sodium bicarbonate (20 ml) and ethyl acetate (60 ml). The organic phase was dried and evaporated in vacuo and the residue purified by FCC eluting with System B (89:10:1) to give a gum. A solution of the gum in methanol (15 ml) was treated with fumaric acid (60 mg) and evaporated in vacuo. The residue was triturated with dry ether to afford the title compound as a colourless powder (381 mg) m.p. 137°-139°.

Analysis: Found: C,56.8; H,6.9; N,8.2; Cl,13.9; $C_{22}H_{31}Cl_2N_3O_2.0.5C_4H_4O_4.0.5H_2O$ requires C,56.8; H,6.75; N,8.3; Cl,13.9%

EXAMPLE 9

4-Amino-3,5-dichloro-α-[[[6-[1-methyl-3-(2-pyridinyl)-propoxy]hexyl]amino]methyl]benzenemethanol, (E)-butenedioate salt (2:1)

4-Amino-3,5-dichloro-α-[[[6-[1-methyl-3-(2-pyridinyl)propoxy]hexyl](phenylmethyl)amino]methyl]benzenemethanol (0.85 g) was hydrogenated according to the method of Example 8. FCC purification of the residue obtained from the ethyl acetate extract eluting with System B (96:3:1→94:5:1) gave an oil (590 mg). A solution of this oil in ethanol (10 ml) was treated with fumaric acid (75 mg) and evaporated in vacuo. Trituration with hexane afforded the title compound as a colourless powder (585 mg) m.p. 113°–115°.

Analysis: Found: C,57.8; H,6.6; N,7.9; Cl,13.6. $C_{23}H_{33}Cl_2N_3O_2.0.5C_4H_4O_4.0.4H_2O$ requires C,57.8; H,6.9; N,8.1; Cl,13.65%.

EXAMPLE 10

4-Amino-3,5-dichloro-α-[[[6-[[6-(pyrazinyl)hexyl]oxy]hexyl]amino]methyl]benzenemethanol A solution of 4-amino-α-(aminomethyl)-3,5-dichlorobenzenemethanol (1.2g), DEA (0.72 ml) and [6-[(6-bromohexyl)oxy]hexyl]pyrazine (1.16 g) in DMF (10 ml) was heated at 100°–110° for 3 h. The resulting dark solution was evaporated in vacuo and the residue purified by FCC eluting with System B (96:2:2→93:5:2) to give the title compound as pale yellow crystals (0.92 g), m.p. 60°–63°.

Analysis: Found: C,59.0; H,7.2; N,11.5; Cl,15.15. $C_{24}H_{36}Cl_2N_4O_2.0.05H_2O$ requires C,59.5; H,7.5; N,11.6; Cl,14.65%.

EXAMPLE 11

4-Amino-3,5-dichloro-α-[[[6-[3-(2-thiazolyl)propoxy]hexyl]amino]methyl]benzenemethanol, (E) butenedioate salt (2:1)

A mixture of 4-amino-α-(aminomethyl)-3,5-dichlorobenzenemethanol (800 mg), 2-[[(6-bromohexyl)oxy]propyl]thiazole (739 mg) and DEA (390 mg) in dry DMF (10 ml) was heated at 80° for 2 h under nitrogen. The solvent was evaporated and the residue purified by FCC eluting with System B (95:5:1) to give the base as a pale yellow oil (615 mg). A solution of the oil in methanol (5 ml) was treated with a solution of fumaric acid (80 mg) in methanol (5 ml). The solvent was evaporated off and the residue triturated under ether (10 ml) to give the title compound as a white powder (560 mg), m.p. 113°–4°.

Analysis: Found: C,51.9; H,5.9; N,8.0; S,6.0; Cl,13.2 $C_{20}H_{29}Cl_2N_3O_2S.0.5C_4H_4O_4.0.5H_2O$ requires C,51.5; H,6.3; N,8.2; S,6.2; Cl,13.8%.

EXAMPLE 12

4-Amino-3,5-dichloro-α-[[[6-[[6-(2-quinolinyl)hexyl]oxy]hexyl]amino]methyl]benzenemethanol A solution of 2-[6-[(6-bromohexyl)oxy]-1-hexynyl]quinoline (1.96 g) in ethanol (100 ml) was hydrogenated over pre-reduced 10% palladium oxide on charcoal catalyst (750 mg). The catalyst was removed by filtration through hyflo and the filtrate evaporated to a brown oil (1.32 g). A solution of 4-amino-α-(aminomethyl)-3,5-dichlorobenzenemethanol (1.05 g) and DEA (0.42 g) in DMF (30 ml) was treated at 90° with a solution of the above brown oil (1.06 g) in DMF (20 ml). The solution was heated to 90°–100° under nitrogen for 3 h, cooled and evaporated in vacuo to a gum. The residue was purified by FCC eluting with System B (98:2:1) to give a pale yellow oil which was triturated with hexane to produce the title compound as a cream coloured powder (1.04 g). m.p. 62.3°–64.7°.

Analysis: Found: C,65.45; H,7.7; N,7.8; Cl,13.9. $C_{29}H_{39}Cl_2N_3O_2$ requires C,65.40; H,7.4; N,8.0; Cl,13.3%.

EXAMPLE 13

4-Amino-3,5-dichloro-α-[[[6-[[6-(2-pyridinyl)hexyl]oxy]hexyl]amino]methyl]benzenemethanol, (E)-butenedioate salt (2:1)

A solution of 4-amino-3,5-dichloro-α-[(phenylmethyl)[6-[[6-(2-pyridinyl)-5-hexynyl]oxy]hexyl]amino]methyl]benzenemethanol (1.65 g) in ethanol (30 ml) was hydrogenated over pre-reduced 10% palladium oxide on charcoal catalyst (650 mg) in ethanol (10 ml) containing hydrochloric acid (conc. hydrochloric acid:ethanol 1:9, 5.27 ml). The mixture was filtered through hyflo and evaporated in vacuo to give an oil which was dissolved in ethyl acetate (120 ml) and washed with 8% sodium bicarbonate solution (100 ml). The organic phase was dried and evaporated in vacuo to an oil and purified by FCC eluting with System A (90:10:1→80:20:1) to give a pale brown oil (750 mg). This was dissolved in methanol (20 ml) and a solution of fumaric acid (91 mg) in methanol (10 ml) was added. The solvent was evaporated to leave the title compound as a pale brown powder which was recrystallised from isopropanol and triturated under ether to give the title compound as a pale brown powder (490 mg), m.p. 100°–102°.

Analysis: Found: C,59.1; H,7.3; N,7.5; Cl,12.7. $C_{25}H_{37}Cl_2N_3O_2.0.5C_4H_4O_4.0.5H_2O$ requires C,59.0; H,7.3; N,7.65; Cl,12.9%.

EXAMPLE 14

4-Amino-3,5-dichloro-α-[[[6-[3-(2-quinolinyl)propoxy]hexyl]amino]methyl]benzenemethanol, (E)-butenedioate salt (2:1)

A solution of 4-amino-α-(aminomethyl)-3,5-dichlorobenzenemethanol (0.76 g), DEA (0.65 ml) in DMF (12 ml) was treated with 2-[3-[(6-bromohexyl)oxy]propyl]quinoline (0.886 g), heated at 115°–120° for 2 h, cooled and evaporated in vacuo. The residue was purified by FCC eluting with System B (96:2:2→94:5:1) to give the free base of the title compound (542 mg), m.p. 44°–49°. This was dissolved in methanol (6 ml) and fumaric acid (64 mg) added. The methanol was removed in vacuo and the residue recrystallised from isopropanol (15 ml) to give the title compound as colourless needles (517 mg), m.p. 121°–122.5°.

Analysis: Found: C,60.6; H,6.2; N,7.5; Cl,12.8. $C_{26}H_{33}Cl_2N_3O_2.0.5C_4H_4O_4.0.5H_2O$ requires C,60.3; H,6.5; N,7.5; Cl,12.7%

The following are examples of suitable formulations of compounds of the invention. The term 'active ingredient' is used herein to represent a compound of the invention.

Tablets

Direct Compression

|  | mg/tablet |
| --- | --- |
| Active ingredient | 2.0 |
| Microcrystalline cellulose USP | 196.5 |
| Magnesium Stearate BP | 1.5 |
| Compression weight | 200.0 |

The active ingredient is sieved through a suitable sieve, blended with the excipients and compressed using 7 mm diameter punches.

Tablets of other strengths may be prepared by altering the ratio of active ingredient to microcrystalline cellulose or the compression weight and using punches to suit.

The tablets may be film coated with suitable film forming materials, such as hydroxypropylmethylcellulose, using standard techniques. Alternatively, the tablets may be sugar coated.

Metered Dose Pressurised Aerosol

Suspension Aerosol

|  | mg/metered dose | Per can |
| --- | --- | --- |
| Active ingredient micronised | 0.100 | 26.40 mg |
| Oleic Acid BP | 0.010 | 2.64 mg |
| Trichlorofluoromethane BP | 23.64 | 5.67 g |
| Dichlorodifluoromethane BP | 61.25 | 14.70 g |

The active ingredient is micronised in a fluid energy mill to a fine particle size range. The oleic acid is mixed with the trichlorofluoromethane at a temperature of 10°–15° C. and the micronised drug is mixed into the solution with a high shear mixer. The suspension is metered into aluminum aerosol cans and suitable metering valves delivering 85 mg of suspension are crimped onto the cans and the dichlorodifluoromethane is pressure filled into the cane through the valves.

| Inhalation Cartridges | mg/cartridge |
| --- | --- |
| Active ingredient micronised | 0.200 |
| Lactose BP to | 25.0 |

The active ingredient is micronised in a fluid energy mill to a fine particle size range prior to blending with normal tabletting grade lactose in a high energy mixer. The powder blend is filled into No. 3 hard gelatin capsules on a suitable encapsulating machine. The contents in the cartridges are administered using a powder inhaler such as the Glaxo Rotahaler.

We claim:

1. A compound of the formula

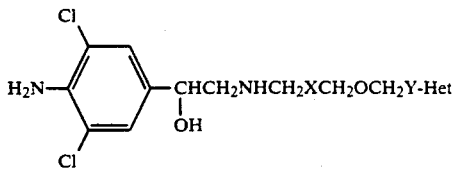

or a physiologically acceptable salt or solvate thereof wherein

X represents a $C_{1-6}$alkylene group,

Y represents a $C_{1-6}$alkylene group, with the proviso that the sum total of carbon atoms in the chains X and Y is not more than 10, and Het represents a pyrimidinyl group, optionally substituted by one or two groups selected from $C_{1-4}$alkyl, $C_{1-4}$alkoxy, hydroxy, halogen, $-NR^3R^4$ and $-COR^8$, wherein $R^3$ and $R^4$ each represent a hydrogen atom or a $C_{1-4}$ alkyl group or $-NR^3R^4$ forms a pyrrolidino, piperidino, hexamethyleneimino, piperazino, N-methylpiperazino, morpholino, homomorpholino or thiomorpholino group; and $R^8$ represents hydrogen, $C_{1-4}$alkoxy or $NR^3R^4$.

2. A compound according to claim 1 wherein X represents $-(CH_2)_3-$ or $-(CH_2)_4-$.

3. A compound according to claim 2 wherein X represents $-(CH_2)_4-$.

4. A compound according to claim 1 wherein Y represents a $C_{2-5}$ alkylene group.

5. A compound according to claim 1 wherein said compound comprises 4-amino-3,5-dichloro-α-[[[6-[-(2-pyrimidinyl)butoxy]hexyl]amino]methyl]benzenemethanol or a physiologically acceptable salt or solvate thereof.

6. A pharmaceutical composition for therapy or prophylaxis of a disease associated with reversible airways obstruction which comprises an effective amount to alleviate said disease of at least one compound as defined in claim 1 or a physiologically acceptable salt or solvate thereof, together with a physiologically acceptable carrier or excipient.

7. A pharmaceutical composition according to claim 6, wherein the disease associated with reversible airways obstruction is asthma or chronic bronchitis.

8. A pharmaceutical composition for the treatment of an inflammatory or allergic skin disease which comprises an effective amount to alleviate said condition of at least one compound as defined in claim 1 or a physiologically acceptable salt or solvate thereof, together with a physiologically acceptable carrier or excipient.

9. A method of therapy or prophylaxis of a disease associated with reversible airways obstruction in a patient, which comprises administering to said patient an effective amount to alleviate said disease of at least one compound as defined in claim 1 or a physiologically acceptable salt or solvate thereof.

10. A method according to claim 9, wherein the disease associated with reversible airways obstruction is asthma or chronic bronchitis.

11. A method of treating a patient suffering from an inflammatory or allergic skin disease which method comprises administering to said patient an effective amount to alleviate said condition of at least one compound as defined in claim 1 or a physiologically acceptable salt or solvate thereof.

* * * * *